United States Patent [19]

Knudsen et al.

[11] Patent Number: 5,214,057
[45] Date of Patent: * May 25, 1993

[54] N-SUBSTITUTED AZAHETEROCYCLIC CARBOXYLIC ACIDS

[75] Inventors: Lars Jacob S. Knudsen, Vedbaek; Anker S. Jorgensen, Copenhagen; Knud E. Andersen, Bagsvaerd; Ursula Sonnewald, Ballerup, all of Denmark

[73] Assignee: Novo Nordisk A/S, Bagsvaerd, Denmark

[*] Notice: The portion of the term of this patent subsequent to Aug. 20, 2008 has been disclaimed.

[21] Appl. No.: 747,322

[22] Filed: Aug. 20, 1991

Related U.S. Application Data

[63] Continuation of Ser. No. 450,805, Dec. 14, 1984, Pat. No. 5,071,859.

[30] Foreign Application Priority Data

Dec. 19, 1988 [DK] Denmark .................. 7044/88

[51] Int. Cl.$^5$ .................. A61K 31/445; C07D 211/60
[52] U.S. Cl. .................. 514/330; 546/227
[58] Field of Search .................. 546/227; 514/330

[56] References Cited

U.S. PATENT DOCUMENTS 4,910,312 3/1990 Pavia .................. 546/227
4,983,614 1/1991 Buzas et al. .................. 514/317

Primary Examiner—Richard L. Raymond
Attorney, Agent, or Firm—Steve T. Zelson; Elias J. Lambiris

[57] ABSTRACT

Novel N-substituted azaheterocyclic carboxylic acids and esters thereof in which an ether group forms part of the N-substituent, the compounds thus having the general formula I

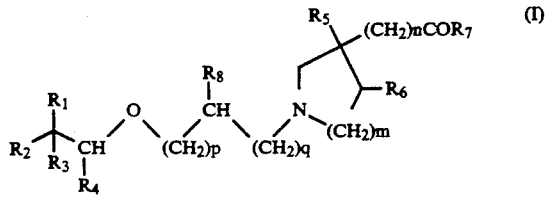

wherein $R^1$ and $R^2$ are the same or different and each represents phenyl, 2-thienyl or 3-thienyl, 2-pyrrolyl- or 3-pyrrolyl, substituted with one or more substituents selected among the following atoms or groups: hydrogen, halogen, $C_{1-6}$-alkyl, $C_{1-6}$-alkoxy or cyano; $R^3$ and $R^4$ each represents hydrogen or together represent a bond; m is 1 or 2 and n is 1 when m is 1 and n is 0 when m is 2; $R^5$ and $R^6$ each represents hydrogen or may—when m is 2—together represent a bond, and $R^7$ is OH or $C_{1-8}$-alkoxy, p is 0 or 1 or 2, q is 0 or 1 or 2, $R^8$ is H and $C_{1-4}$-alkyl, are potent inhibitors of GABA uptake from the synaptic cleft.

5 Claims, No Drawings

N-SUBSTITUTED AZAHETEROCYCLIC CARBOXYLIC ACIDS

This is a continuation application of co-pending application Ser. No. 07/450,805, filed Dec. 14, 1989, now U.S. Pat. No. 5,071,859.

The present invention relates to novel N-substituted azaheterocyclic carboxylic acids and esters thereof, in which an alkyl ether group forms part of the N-substituent and salts thereof, to methods for their preparation, to compositions containing them, and to their use for the clinical treatment of abnormal function of γ-aminobutyric acid neurotransmission system.

In recent years much pharmacological research concerning γ-aminobutyric acid (hereinafter designated GABA), an inhibitory neurotransmitter in the mammalian central nervous system, has been carried out.

The inhibition of GABA uptake results in enhanced availability of this inhibitory neurotransmitter in the synaptic cleft and thus to increased GABA'ergic activity. Increased GABA'ergic activity can be useful in the treatment, e.g. of anxiety, pain and epilepsy, as well as muscular and movement disorders (see for example Krogsgaard-Larsen, P. et al., Progress in Medicinal Chemistry 22 (1985) 68-11, Advances in Drug Research, 17 (1988), 381-456.

A well-known and potent inhibitor of GABA uptake from the synaptic cleft into presynaptic nerve terminals and glial cells is, for example, piperidine-3-carboxylic acid (nipecotic acid) However, being a relatively polar compound and therefore unable to cross the blood-brain barrier, piperidine-3-carboxylic acid itself has found no practical utility as a drug.

In U.S. patent specifications No. 4,383,999 and No. 4,514,414 (SmithKline Beckman Corporation) and European patent applications No. 86903274 and No. 87300064 (Novo Industri A/S) some derivatives of N-(4,4-disubstituted-3-butenyl)azaheterocyclic carboxylic acids are claimed as inhibitors of GABA uptake. In Danish patent application No. 2704/88 (Novo Industri A/S) N-substituted azaheterocyclic carboxylic acids in which an oxime ether group forms part of the N-substituent are claimed as inhibitors of GABA uptake. European patent application No. 86115478.9 (Warner-Lambert Company) claims that 1-aryloxyalkylpyridine-3-carboxylic acids are inhibitors of GABA uptake.

According to Yunger, L.M. et al., J. Pharm. Exp. Therap., 228 (1984) 109, N-(4,4-diphenyl-3-butenyl)-nipecotic acid (designated SK&F 89976A), N-(4,4-diphenyl-3-butenyl)guvacine (designated SK&F 100330A), N-(4,4-diphenyl-3-butenyl)homo-β-proline (designated SK&F 100561) and N-(4-phenyl-4-(2-thienyl)-3-butenyl)nipecotic acid (designated SK&F 100604J) are orally active inhibitors of GABA uptake. These data are summarized in Krogsgaard-Larsen, P. et al., Epilepsy Res., 1 (1987) 77-93.

Nipecotic acid is piperidine-3-carboxylic acid, guvacine is 1,2,5,6-tetrahydropyridine-3-carboxylic acid and homo-β-proline is pyrrolidine-3-acetic acid.

The present invention relates to novel N-substituted azaheterocyclic carboxylic acids and esters thereof in which an ether group forms part of the N-substituent. The compounds according to the invention have the general formula I

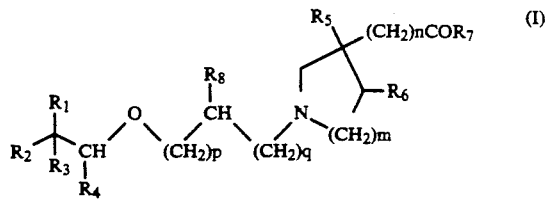

wherein $R^1$ and $R^2$ are the same or different and each represents phenyl, 2-pyrrolyl or 3-pyrrolyl, 2-thienyl or 3-thienyl, substituted with one or more substituents selected among the following atoms or groups: hydrogen, halogen, $C_{1-6}$-alkyl, $C_{1-6}$- alkoxy or cyano; $R^3$ and $R^4$ each represents hydrogen or together represent a bond; m is 1 or 2 and n is 1 when m is 1 and n is 0 when m is 2; $R^5$ and $R^6$ each represents hydrogen or may - when m is 2 - together represent a bond, and $R^7$ is OH or C p is 0 or 1 or 2, q is 0 or 1 or 2, $R^8$ is H and $C_{1-4}$-alkyl. When $R^1$ and/or $R^2$ is pyrrolyl the substituent on the N-atom can be either hydrogen or $C_{1-4}$- alkyl. The compounds according to the invention may optionally exist as pharmaceutically acceptable acid addition salts or—when the carboxylic acid group is not esterified—as pharmaceutically acceptable metal salts or—optionally alkylated—ammonium salts. The compounds of formula I have a greater lipophilicity—and thus a greater availabililty to the brain—as well as a far higher affinity to the GABA uptake sites than the parent compounds without the N-substituent (e.g. pyrrolidine-3-acetic acid (homo-β-proline), piperidine-3-carboxylic acid (nipecotic acid) and 1,2,5,6-tetrahydropyridine-3-carboxylic acid (guvacine)). They therefore possess interesting and useful pharmacological properties.

The compounds of formula I may exist as geometric and optical isomers and all isomers and mixtures thereof are included herein. Isomers may be separated by means of standard methods such as chromatographic techniques or fractional crystallization of salts with optically active acids or bases.

It has been demonstrated that the novel compounds of the general formula I, which inhibit the uptake of GABA from the synaptic cleft possess useful pharmacological properties on the central nervous system, in that they cause a selective enhancement of GABA'ergic activity. Compounds of formula I may be used to treat, for example, pain, anxiety, epilepsy and certain muscular and movement disorders. They may also find use as sedatives, hypnotics and antidepressants.

Pharmaceutically acceptable acid addition salts of compounds of formula I include those derived from inorganic or organic acids such as hydrochloric, hydrobromic, sulfuric, phosphoric, acetic, lactic, maleic, phthalic, citric and fumaric acid.

The compounds according to the invention are prepared according to one of the following methods:

METHOD A

Compounds having the general formula Ia i.e. compounds of the general formula I as defined above in which $R^3$ and $R^4$ together form a bond may be prepared by the following method A:

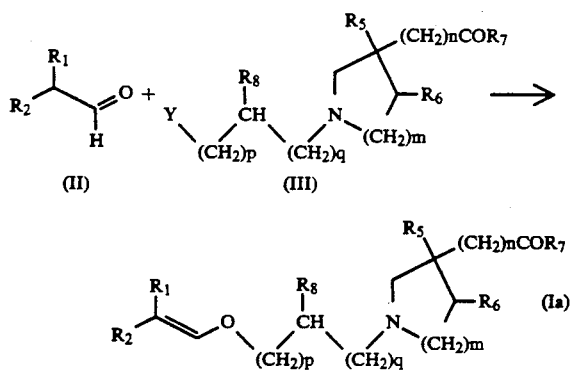

An acetaldehyde derivative of formula II wherein $R^1$ and $R^2$ are as defined above is allowed to react with a compound of formula III wherein Y is a suitable leaving group such as halogen or p-toluene sulphonate. This reaction may be carried out in a suitable solvent such as tetrahydrofuran, toluene or N,N-dimethylformamide in the presence of a strong base such as sodium hydride at a temperature up to reflux temperature for e.g. 1 to 72 h (for examples of the synthesis of acetaldehyde derivatives of formula II, see Meyers, A.I. et al., J. Amer. Chem. Soc., 104 (1982) 877-9 Matteson, D.S. et al., J. Org. Chem., 45 (1980) 1091-5). Blicke, F.F. and Faust, J.A., J. Amer. Chem. Soc., 16 (1954), 3156; Borch R.F., Tetrahedron Lett., 36, (1972), Martin, S.F., Synthesis, (1979), 633; Ashwood M.S. et al., Synthesis, (1988), 379)).

METHOD B

Compounds having the general formula I as defined above may be prepared by the following general method B:

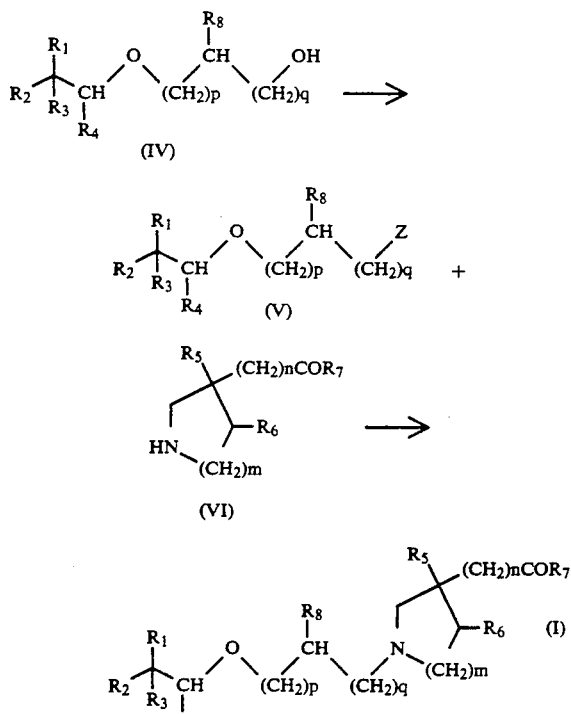

A hydroxy ether derivative of general formula IV wherein $R^1$, $R^2$, $R^3$, $R^4$, $R^8$, p and q are as defined above, is allowed to react to form a compound of formula V, wherein $R^1$, $R^2$, $R^3$, $R^4$, $R^8$, p and q are as defined above and Z is a suitable leaving group (i.e. halogen, tosylate, mesylate). This reaction may be carried out in a suitable solvent (e.g. dichloromethane, toluene, pyridine) with the appropriate reagent (e.g. p-toluenesulphonyl chloride, phosphorus oxychloride, phosphorus pentachloride thionyl halide, phosphorus tribromide or methanesulphonyl chloride) at a temperature up to reflux temperature for e.g. 1 to 72 h. The ether derivative of formula V, wherein $R^1$, $R^2$, $R^3$, $R^4$, $R^8$, Z, p and q are as defined above is allowed to react with an amino acid derivative of formula VI wherein $R^5$, $R^6$, $R^7$, n and m are as defined above, to form a compound of general formula I. This reaction may be carried out in a suitable solvent such as acetone, tetrahydrofuran, toluene or N,N-dimethylformamide in the presence of a base such as an alkali metal carbonate or a suitable tertiary amine at a temperature up to reflux temperature for e.g. 1 to 72 h.

METHOD C

Compounds having the general formula Ia as defined above (Method A) may be prepared by the following Method C:

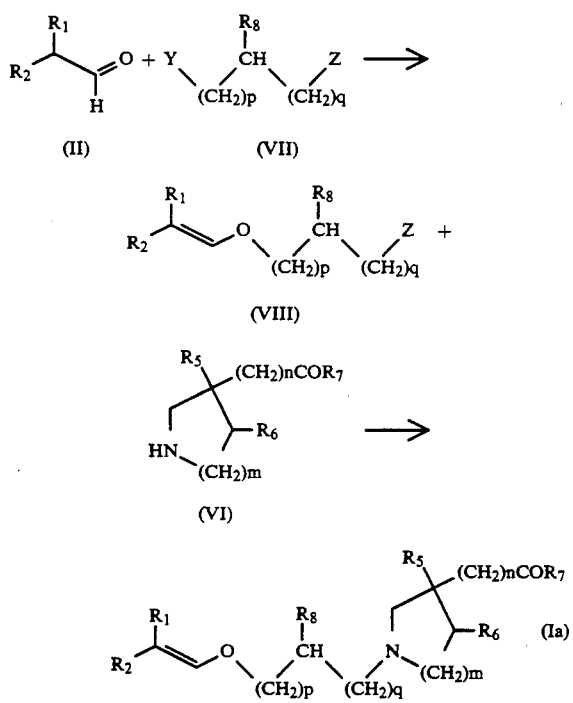

An acetaldehyde derivative of formula II las defined in Method A) is allowed to react with a disubstituted alkane of formula VII, wherein $R^8$, p and q are as defined above and Y and Z are suitable leaving groups (such as halogen, tosylate or mesylate) (Y and Z may be the same or different) to form a vinyl ether derivative of formula VIII. This reaction may be carried out in a suitable solvent such as tetrahydrofuran, toluene or N,N-dimethylformamide in the presence of a strong base, such as sodium hydride or an alkyllithium at a temperature up to reflux temp. for e.g. 1 to 72 h.

The vinyl ether derivative of formula VIII is allowed to react with an amino acid derivative of formula VI (in much the same way as compound V reacts with VI in Method B) to form a compound of general formula Ia, wherein $R^1$, $R^2$, $R^5$, $R^6$, $R^7$, $R^8$, n, m, p and q are as defined above.

METHOD D

Compounds having the general formula Ia as defined above (Method A) may be prepared by the following method D:

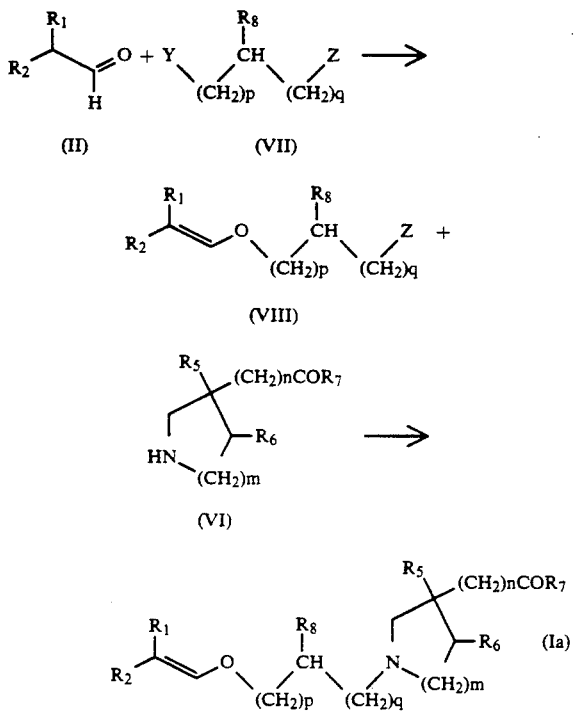

This method is superficially similar to Method C, but with the important difference that the vinyl ether derivative of formula VIII is prepared by a phase-transfer reaction of the aldehyde derivative (II) with the disubstituted alkane of formula VII. The substituents are as defined in Method C.

Examples of such phase transfer alkylations may be found in W. E. Keller, *Phase Transfer Reactions*, Vol. 1 and 2, Fluka, Georg Thieme Verlag, Stuttgart 1986 and 1989.

METHOD E

Compounds having the general formula Ib, i.e. compounds of the general formula I as defined above, in which $R^3$, $R^4$, $R^5$ and $R^6$ are all hydrogen and m is 2 and n is O, can be prepared by hydrogenating compounds of formula Ia:

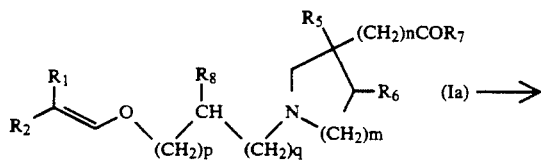

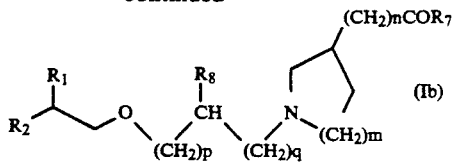

The hydrogenation is preferably carried out at room temperature in the presence of a hydrogenation catalyst such as a noble metal catalyst, e.g. palladium on charcoal. The preferred hydrogen pressure is from atmospheric pressure up to about 5 atm., however, the hydrogenation can also be performed at high pressure. Ethanol and methanol are examples of preferred solvents.

Under certain circumstances it may be necessary to protect the intermediates used in the above methods (e.g. III or V) with suitable protecting groups. The carboxylic acid group can for example be esterified. Introduction and removal of such groups is described e.g. in "*Protective Groups in Organic Chemistry*"J. F. W. McOrnie ed. (New York, 1973).

If esters have been prepared in methods A-E, compounds of formula I wherein $R^7$ is OH may be prepared by hydrolysis of the ester group, preferably at room temperature in a mixture of an aqueous alkali metal hydroxide solution and an alcohol such as methanol or ethanol, for example for about 0.5 to 6 h.

PHARMACOLOGICAL METHODS

Values for in vitro inhibition of [$^3$H]-GABA uptake for these compounds were assessed essentially by the method of Fjalland (*Acta Pharmacol. Toxicol.* 42 (1978) 73–76).

Male Wistar rat cortical tissue was gently homogenized by hand using a glass/PTFE homogenizer in 10 volumes of 0.32 M sucrose. Incubation was performed in a 40 mM tris HCl buffer (pH 7.5 at 30° C.) containing 120 nM NaCl, 9.2 nM KCl, 4 mM MgSO$_4$, 2.3 mM CaCl$_2$ and 10 mM glucose, for 60 min. at 30° C. Ligand concentration was 0.2 nM.

Values for inhibition of GABA uptake for some representative compounds are recorded in the table below.

TABLE 1

| Inhibition of [$^3$H]-GABA uptake | |
|---|---|
| Product from Example No. | IC$_{50}$ (nm) in vitro |
| 2 | 104 |
| 12 | 8 |
| 13 | 26 |
| 33 | 127 |
| 14 | 30 |
| 17 | 15 |
| 23 | 47 |
| 30 | 12 |

Compounds of formula I are useful because they possess significant pharmacological activity in man. In particular the compounds of formula I are useful as a consequence of their inhibition of GABA uptake.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent. No toxic effects have been observed.

The compounds of formula I may be administered in pharmaceutically acceptable acid addition salt form or where possible as a metal or a lower alkylammonium salt. Such salt forms exhibit approximately the same order or activity as the free base forms.

This invention also relates to pharmaceutical compositions comprising a compound of formula I or a pharmaceutically acceptable salt thereof and, usually such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder of pellet form, or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

The pharmaceutical compositions of this invention can be made following the conventional techniques of the pharmaceutical industry involving mixing, granulating and compressing or variously mixing and dissolving the ingredients as appropriate to give the desired end product.

The route of administration may be any route, which effectively transports the active compound to the appropriated or desired site of action, such as oral or parenteral, the oral route being preferred.

A typical tablet which may be prepared by conventional tabletting techniques contains:

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |
| HPMC | approx. 9 mg |
| *Mywacett ® 9-40 T | approx. 0.9 mg |

*Acylated monoglyceride used as plasticizer for film-coating

The route of administration may be any route which effectively transports the active compound to the appropriate or desired site of action, such as oral or parenteral, the oral route being preferred.

EXAMPLES

The process for preparing compounds of formula I and preparations containing them is further illustrated in the following examples which, however, are not to be construed as limiting. The examples illustrate some preferred embodiments.

Hereinafter, TLC is thin layer chromatography, THF is tetrahydrofuran, TFA is trifluoroacetic acid and m.p. is melting point. The structures of the compounds are confirmed by NMR and elemental analysis. Where melting points are given, these are uncorrected. All temperatures are in ° C. Compounds used as starting materials are either known compounds or compounds which can readily be prepared by methods known per se. Novel diarylacetaldehydes were prepared by known methods (see e.g. Blicke, FF and Faust, J.A., J. Amer. Chem. Soc., 16 (1954), 3156; Borch R.F., *Tetrahedron Lett.* 36, (1972), 3761; Martin, S.F., *Synthesis*, (1979), 633; Ashwood M.S. et al., *Synthesis*, (1988), 379); Meyers, A.I., et al., *J. Amer. Chem. Soc.*, 104 (1982), 877-9; Matteson, D.S., et al., *J. Org. Chem.*, 45 (1980) 1091-5)). Column chromatography was carried out using the technique described by Still, W.C. et al., *J. Org. Chem.*, 43 (1978) 2923 on Merck silica gel 60 (Art. 9385). HPLC was carried out using a Waters model 510 chromatograph interfaced via a system module to a Waters 490 multiwavelength detector to a reversed phase $C_{18}$ column (250 × 4 mm, 5 μm, 100 Å. Retention times are given in minutes.

EXAMPLE 1

Method A (R)-1-[2-[[2,2-Diphenylethenyl]oxy]ethyl]-3-piperidine carboxylic acid ethyl ester The (R)-enantiomer of ethyl nipecotate (100 g, 0.64 mole) (Akkerman, A.M. et al., *Gazz.Chim.Ital.*, 102 (1972) 189) was mixed in dry acetone (300 ml) with 2-bromoethanol (85 g, 0.68 mole), dried, powdered potassium carbonate (188 g, 1.28 mole) and potassium iodide (21.6 g, 0.13 mole). The reaction mixture was stirred at room temperature for 18 h and at reflux for 24 h. Filtration of the reaction mixture and evaporation of the resultant filtrate gave (R)-1-(2-hydroxyethyl)nipecotic acid ethyl ester as an oil, which was purified by distillation in vacuo (110°-° C., 0.1 mmHg), yield (72.2 g, 56%). TLC: rf 0.20 (SiO₂; dichloromethane/methanol 19/1).

A sample of the above alcohol (140 g, 0.70 mole) was dissolved in toluene (400 ml) and thionyl bromide (80 ml, 0.77 mole) was introduced with vigorous stirring. After 1.5 h the exotherm reaction had subsided and diethyl ether (400 ml) was added. The resultant precipitate was collected by filtration and washed with diethyl ether. The solid was triturated with ethyl acetate, again collected on a filter and dried to provide (R)-1-(2-bromoethyl)nipecotic acid ethyl ester hydrobromide (175 g, 73%) as a white solid, m.p. 210°-215° C.

Diphenylacetaldehyde (4.9 g, 0.025 mole) was added dropwise to a mixture of sodium hydride (1.5 g, 0.05 mole, 80% oil dispersion) and dry toluene (25 ml) at 0° C. This mixture was stirred at room temperature for 0.5 h, heated to 50° C. and allowed to cool to room temperature. The above (R)-1-(2-bromoethyl)nipecotic acid ethyl ester hydrobromide (8.6 g, 0.025 mole) was added portionwise whilst the temperature was kept below 30° C. with an ice-water bath. After being stirred for 1 h the reaction mixture was filtered, and the filtrate was evaporated to dryness. Flash chromatography of the residue on silica gel (200 g) using a mixture of heptane and tetrahydrofuran (4/1) as eluent provided the title compound (6.6 g, 69%) as an oil. Tlc: rf 0.24 (SiO$_2$; heptane/THF 7/3).

EXAMPLE 2

(R)-1-[2-[[2,2-Diphenylethenyl]oxy]ethyl]-3-piperidine carboxylic acid hydrochloride (R)-1-[2-[[2,2-Diphenylethenyl]oxy]ethyl]-3-piperidine carboxylic acid ethyl ester (example 1) (3.0 g, 0.079 mol) was dissolved in ethanol (20 ml) and 12 N sodium hydroxide solution (2.0 ml) was introduced. After stirring the solution at room temperature for 2.5 h, 37% hydrochloric acid (ca. 2.2 ml) was added, with acidity measured at pH 2. Dichloromethane (300 ml) was introduced, and the mixture was dried (MgSO$_4$). Filtration and evaporation of the filtrate gave a solid, which was triturated with diethyl ether, to give the title compound (2.65 g, 86%) as a white solid, m.p. 210°–216° C.

C$_{22}$H$_{25}$ClNO$_3$.HCl requires: C, 68.1; H, 6.8; N, 3.6; Cl, 9 15. Found: C, 67.6; H, 6.7; N, 3.65; Cl, 9.0%.

EXAMPLE 3

Z-(R)-1-[2-[[2-(2-Methylphenyl)-2-phenylethenyl]oxy]ethyl]-3-piperidine carboxylic acid hydrochloride Z-(R)-1-[2-[[2-(2-Methylphenyl)-2-phenylethenyl]oxy]ethyl]-3-piperidine carboxylic acid ethyl ester (2.0 g, 0.0051 mol) (prepared as described in Method A) was dissolved in ethanol (8 ml) and 12N sodium hydroxide solution (1.3 ml) was introduced. After stirring the solution at room temperature for 2 h, 37% hydrochloric acid (ca. 1.8 ml) was added with cooling, followed by dichloromethane (300 ml) and the mixture was dried (Na$_2$SO$_4$). Filtration and evaporation of the filtrate gave a residue, which was co-evaporated with acetone. The solid product was triturated with ethyl acetate, collected by filtratiion and dried in vacuo to give the title compound (0.70 g, 34%), m.p. 206°–211° C.

C$_{23}$H$_{27}$NO$_3$.HCl requires C, 68.7; H, 7.0; N, 3.5; Cl, 8.8. Found: C, 67.7; H, 7.1; N, 3.5; Cl, 8.9%

EXAMPLE 4

E-(R)-1-[2-[[2-(2-Methylphenyl)-2-phenylethenyl]oxy]ethyl]-3-piperidine carboxylic acid hydrochloride E-(R)-1-[2-[[2-(2-Methylphenyl)-2-phenylethenyl]oxy]ethyl]-3-piperidine carboxylic acid ethyl ester (1.1 g, 0.0028 mol) (prepared as described in Method A) was dissolved in ethanol (5 ml) and 12N sodium hydroxide solution (0.7 ml) was introduced. After stirring the solution at room temperature for 2h, 37% hydrochloric acid solution (ca. 1.0 ml) was added (with cooling) followed by dichloromethane (300 ml) and the mixture was dried (Na$_2$SO$_4$). Filtration and evaporation of the filtrate gave a residue, which was co-evaporated with acetone. The solid product was triturated with ethyl acetate, collected by filtration and dried in vacuo to provide the title compound (0.70 g, 62%), m.p. 195–196.

C$_{23}$H$_{27}$NO$_3$.HCl requires C, 68.7; H, 7.0; N, 3.5; Cl, 8.8 Found: C, 68.1; H, 7.2; N, 3.4; Cl, 8.7%.

EXAMPLE 5

E or Z-(R)-1-[2-[[2-(2-Chlorophenyl)-2-phenylethenyl]oxy]ethyl]-3-piperidine carboxylic acid hydrochloride E or Z-(R)-1-[2-[[2-(2-Chlorophenyl)-2-phenylethenyl]oxy]-ethyl]-3-piperidine carboxylic acid ethyl ester (1.0 g, 0.0024 mol) (prepared as described in Method A) was dissolved in ethanol (10 ml) and 10N sodium hydroxide solution (2.42 ml) was introduced. After stirring the solution at room temperature for 5 h, water (100 ml) was added and the mixture was neutralized with 2N hydrochloric acid solution. Evaporation of ethanol under reduced pressure gave an aqueous solution, which was acidified to pH 0.5 with 2N hydrochloric acid solution and extracted with dichloromethane (4 × 100 ml). The combined extracts were dried (Na$_2$SO$_4$) and evaporated to an oil, which was dissolved in a trace of methanol. Toluene (20 ml) was introduced, and the product solution was heated on a steam bath. On cooling the title compound (0.64 g, 62%), a white crystalline solid, was collected and dried in vacuo. M.p. softens at 170°, melts at 198°.

C$_{22}$H$_{23}$ClNO$_3$.HCl requires C, 62.6; H, 5.7; N, 3.2; Cl, 16.8 Found: C, 62.5; H, 6.0; N, 3.2; Cl, 16.6%.

EXAMPLE 6

E or Z-(R)-1-[2-[[2-(2-Chlorophenyl)-2-phenylethenyl]oxy]-ethyl]-3-piperidine carboxylic acid hydrochloride E or Z-(R)-1-[2-[[2-(2-Chlorophenyl)-2-phenylethenyl]oxy]-ethyl]-3-piperidine carboxylic acid ethyl ester (1.0 g, 0.0024 mol) (opposite geometric isomer of example 6) was dissolved in ethanol (20 ml) and 10N sodium hydroxide solution (2.42 ml) was introduced. After stirring the reaction mixture at room temperature for 16 h, water (100 ml) was added and the mixture was neutralized with 2N hydrochloric acid solution Evaporation of ethanol under reduced pressure gave an aqueous solution, which was acidified to pH 1 with 2N hydrochloric acid and extracted with dichloromethane (4 × 100 ml). The combined extracts were dried (Na$_2$SO$_4$) and evaporated to a solid, which was recrystallized from methanol/toluene to give the title compound (0.58 g, 56%) as white crystals (after drying in vacuo), m.p. 227°–8°.

C$_{22}$H$_{23}$ClNO$_3$.HCl requires C, 62.6; H, 5.7; N, 3.3; Cl, 16.8 Found: C, 62.6; H, 6.1; N, 3.2; Cl, 16.7%.

EXAMPLE 7

(R)-1-[3-[[2,2-Diphenylethenyl]oxy]propyl]-3-piperidine carboxylic acid hydrochloride (R)-1-[3-[[2,2-Diphenylethenyl]oxy]propyl]-3-piperidine carboxylic acid ethyl ester (0.60 g, 0.0015 mol) (prepared as described in Method A) was dissolved in ethanol (5 ml) and 12N sodium hydroxide solution (0.4 ml) was introduced. After stirring the solution at room temperature for 2 h, 37% hydrochloric acid (ca. 0.52 ml) was added with cooling followed by dichloromethane (250 ml). The mixture was dried (Na$_2$SO$_4$). Filtration and evaporation of the filtrate gave a residue, which was co-evaporated with acetone. The solid product was triturated with acetone, collected by filtration and dried in vacuo to give the title compound (0.30 g, 50%), m.p. 176°–180°.

$C_{23}H_{27}NO_3 \cdot HCl \cdot 0.25H_2O$ requires C, 68.0; H, 7.1; N, 3.45; Cl, 8.7 Found: C, 67.9; H, 7.1; N, 3.4; Cl, 8.3%

EXAMPLE 8

(R)-1-[2-[[2-(2-Methylphenyl)-2-(3-methyl-2-thienyl) etheyl]oxy]ethyl]-3-piperidine carboxylic acid hydrochloride (R)-1-[2-[[2-(2-Methylphenyl)-2-(3-methyl-2-thienyl) ethenyl]oxy]ethyl]-3-piperidine carboxylic acid ethyl ester (6.0 g, 0.0133 mol) (prepared as described in Method A) was dissolved in ethanol (100 ml) and 10N sodium hydroxide solution (13.3 ml) was introduced. After stirring the solution at room temperature for 3 h water (200 ml) was added, and the ethanol was evaporated under reduced pressure. The aqueous solution was acidified to pH 1 with 2N hydrochloric acid solution and extracted with dichloromethane (4 × 150 ml). The combined extracts were dried (MgSO$_4$) and evaporated to a solid, which was recrystallized from methanol/toluene/cyclohexane to give the title compound (4.09 g, 68%) as white crystals, m.p. 207°–12° (after drying in vacuo).

$C_{22}H_{27}NO_3S \cdot HCl \cdot 0.33PhCH_3$ requires C, 64.6; H, 6.8; N, 3.1; Cl, 7.8; S, 7.6 Found: C, 64.6; H, 6.8; N, 3.1; Cl, 7.8; S, 7.3%.

EXAMPLE 9

E or Z-(R)-1-[2-[[2-(3-Fluorophenyl)-2-(2-methylphenyl) ethenyl]oxy]ethyl]-3-piperidine carboxylic acid hydrochloride E or Z-(R)-1-[2-[[2-(3-Fluorophenyl)-2-(2-methylphenyl)-ethenyl] oxy]ethyl]-3-piperidine carboxylic acid ethyl ester (0.40 g, 0.00097 mol) (prepared as described in Method A) was dissolved in ethanol (5 ml) and 12 N sodium hydroxide solution (0.3 ml) was introduced. After stirring the solution at room temperature for 5 h, 37% hydrochloric acid solution was added until the pH was measured as ca. 1. Dichloromethane (250 ml) was introduced, and the resultant precipitate was dissolved by addition of ice portionwise with vigorous stirring. The organic phase was separated, dried (Na ) and evaporated to a residue, which was co-evaporated with acetone. Recrystallization from acetone provided the title compound (0.10 g, 24%) as a white solid, m.p. 193°–195°.

$C_{23}H_{26}FNO_3 \cdot HCl$ requires C, 65.8; H, 6.5; N, 3.3; Cl, 8.4. Found: C, 65.4; H, 6.6; N, 3.7; Cl, 8.2%.

EXAMPLE 10

Z or E-(R)-1-[2-[[2-(3-Fluorophenyl)-2-(2-methylphenyl) ethenyl]oxy]ethyl]-3-piperidine carboxylic acid hydrochloride Z or E-(R)-1-[2-[[2-(3-Fluorophenyl)-2-(2-methylphenyl)ethenyl]oxy]ethyl]-3-piperidine carboxylic acid ethyl ester (0.50 g, 0.22123 mol) (prepared as described in Method A) (opposite geometric isomer of example 9) was dissolved in ethanol (5 ml) and 12 N sodium hydroxide solution (0.3 ml) was introduced. After stirring the solution at room temperature for 5 h, 37% hydrochloric acid solution was added until the pH was measured as ca. 1. Dichloromethane (250 ml) was introduced, and the resultant precipitate was dissolved by addition of ice with vigorous stirring. The organic phase was separated, dried (Na$_2$SO$_4$) and evaporated to a residue, which was co-evaporated with acetone. Recrystallization from acetone provided the title compound (0.10 g, 20%) as a white solid, m.p. 193°–195°

$C_{23}H_{26}FNO_3 \cdot HCl$ requires C, 65.8; H, 6.5; N, 3.3, Cl, 8.4 Found: C, 65.5; H, 6.6; N, 3.5; Cl, 8.3%.

EXAMPLE 11

Method B (R)-1-[2-[[2,2-bis(3-Methyl-2-thienyl)ethenyl]oxy]ethyl]-3-piperidine carboxylic acid ethyl ester 2-(Triphenylmethoxy)ethanol (3.98 g, 0.013 mol) was dissolved in dry THF (50 ml) and a 2.5 M solution of butyllithium in hexane (5.5 ml, 0.0137 mol) was added at 0° C. A solution of bromoacetic acid (1.81 g, 13.0 mmol) was separately treated with a 2.5 M solution of butyllithium in hexane (5.5 ml, 13.7 mmol) at 0° C. before the two solutions were mixed. This reaction mixture was heated at reflux for 68 h, cooled, and water (200 ml) was added. Washing with ethyl acetate was followed by acidification of the aqueous phase with 0.5 M citric acid solution (50 ml). Extraction with ethyl acetate (2 × 100 ml) and drying (MgSO$_4$) provided crude [2-(triphenylmethoxy)ethoxy]acetic acid (2.78 g, 58%). This acid was dissolved in dichloromethane (30 ml) and dicyclohexylcarbodiimide (1.72 g, 0.0083 mol) was added, followed by 4-pyrrolidinopyridine (0.11 g, 0.00074 mol) and ethanol (0.89 ml, 2 equiv.) (A. Hassner et al., *Tetrahedron Lett.* (1978) 4475). The reaction mixture was stirred for 16 h at room temperature and filtered to remove dicyclohexyl urea. The filtrate was evaporated, and the residue was purified by flash chromatography on silica gel (3 × 20 cm). Elution with cyclohexane containing 1–3% ethyl acetate provided the desired [2-(triphenylmethoxy)ethoxy]acetic acid ethyl ester (1.5 g, 50%) as an oil.

2-Bromo-3-methylthiophene (1.5 g, 0.0085 mol) and magnesium turnings (0.22 g) were heated gently in dry THF (30 ml) and the reaction rapidly became exothermic. After 0.2 h the reaction mixture was heated at reflux for 0.5 h, and the above ester (1.5 g, 0.0038 mol) was introduced as a solution in THF (20 ml). The mixture was again heated at reflux for 0.5 h, cooled, and ammonium chloride solution (100 ml) was added. Stirring for 0.5 h at room temperature was followed by extraction with ethyl acetate (3 × 70 ml). The combined extracts were dried (MgSO$_4$) and evaporated. The residue was dissolved in a mixture of 2 N hydrochloric acid (50 ml), THF (50 ml) and ethanol (50 ml) and the solution was heated at 50° C. for 1 h, and basified to pH 9 5 with sodium hydroxide solution The organic solvents were removed in vacuo and the aqueous residue was extracted with ethyl acetate (3 × 75 ml). Drying of the combined extracts (MgSO$_4$) and evaporation gave an oil, which was purified by flash chromatography on silica gel (2 × 15 cm). Elution with cyclohexane/ethylacetate (9/1) provided 2-[2-(2-Hydroxyethoxy)-1-(3-methyl-2-thienyl)ethenyl]-3-methylthiophene (0.54 g, 50%) as a gum.

The above alcohol (0.53 g, 0.0019 mol) was dissolved in dry toluene (20 ml) and the solution was cooled to 0° C. A solution of n-butyllithium (2.5 M in hexane) (0.9 ml, 0.0023 mol) was introduced, and the reaction mixture was allowed to stand at 0° C. for 1 h after which time a solution of p-toluenesulphonyl chloride (0.47 g, 0.0025 mol) in toluene (10 ml) was added. The mixture was left at room temperature for 20 h and to the resulting tosylate solution was added the (R)-enantiomer of ethyl nipecotate (0.59 g, 0.0038 mol) and powdered, dried potassium carbonate (1.04 g, 0.0075 mol). The temperature was increased to 80° C. and maintained for 50 h. The reaction mixture was cooled and water (50 ml) was added. The toluene phase was separated and the water phase was extracted with ethyl acetate (50 ml). The combined organic extracts were dried (MgSO$_4$) and evaporated to give an oil, which was purified by flash chromatography on silica gel. Elution with cyclohexane/ethyl acetate (19/1–5/1) provided the title compound (0.25 g, 31%) as a gum. TLC: rf 0.26 (SiO2; heptane/THF 7/3).

EXAMPLE 12

(R)-1-[2-[[2,2-bis(3-Methyl-2-thienyl)ethenyl]oxy]ethyl]-3-piperidine carboxylic acid (R)-1-[2-[[2,2-bis(3-Methyl-2-thienyl)ethenyl]oxy]ethyl]-3-piperidine carboxylic ethyl ester (420 mg, 1 mmol) (example 11) was dissolved in ethanol (20 ml) and 10 N sodium hydroxide solution (1.00 ml) was introduced. After 3 h at room temperature the pH of the solution was adjusted to 9 with 2 N hydrochloric acid. The ethanol was removed by evaporation and the pH of the solution was adjusted to 2.5. Extraction with dichloromethane (4 × 15 ml), drying of the combined extracts (MgSO$_4$) (charcoal decolourisation) and evaporation of the filtrate provided a residue, which was recrystallized from water. This provided the title compound (0.34 g, 84%) as a cream solid, m.p. 55°–70° C. TLC: rf 0.37 (SiO$_2$, CH$_2$Cl$_2$/MeOH 1/1).

C$_{20}$H$_{25}$NO$_3$S$_2$.3/4 H$_2$O requires C, 59.3; H, 6.6; N, 3.45; S, 15.8; Cl, 2.9. Found: C, 59.3; H, 6.6; N, 3.5; S, 15.85%.

EXAMPLE 13

1-[2-[[2,2-bis(2-Methylphenyl)ethenyl]oxy]ethyl]-1,2,5,6-tetrahydro-3-pyridine carboxylic acid hydrochloride 1-[2-[[2,2-bis(2-Methylphenyl)ethenyl]oxy]ethyl]-1,2,5,6-tetrahydropyridine-3-carboxylic acid methyl ester (0.70 g, 0.0018 mol) (prepared as described in Method B) was dissolved in ethanol (30 ml) and 10 N sodium hydroxide solution (1.79 ml) was introduced. The reaction mixture was stirred at room temperature for 2.5 h and water (100 ml) was added, followed by 2 N hydrochloric acid solution to pH 10. Ethanol was removed by evaporation under reduced pressure, and the aqueous solution was washed with ethyl acetate (20 ml). The aqueous phase was separated, acidified to pH 2 with 2 N hydrochloric acid solution, and extracted with dichloromethane (4 × 50 ml). The combined extracts were dried (MgSO$_4$) and the residue was crystallized from propanol/toluene to give the title compound (0.53 g, 76%), m.p. 195°–198°.

C$_{24}$H$_{27}$NO$_3$.HCl requires C, 69.65; H, 6.8; N, 3.4; Cl, 8.55 Found: C, 69.6; H, 6.85; N, 3.2; Cl, 8.1%.

EXAMPLE 14

Method C a.

1-[2-(2-Bromoethoxy)-1-(2-methylphenyl)ethenyl]-4-fluoro-2-methylbenzene (4-Fluoro-2-methylphenyl)-(2-methylphenyl)acetaldehyde (3.5 g, 0.0144 mol) was dissolved in dry THF (20 ml) and added dropwise to a suspension of sodium hydride (60% oil dispersion) (0.63 g, 0.0158 mol) in dry tetrahydrofuran (30 ml). The mixture was stirred at room temperature for 1 h and heated at reflux for 0.5 h. After cooling 1,2-dibromoethane (12.4 ml, 10 equiv.) was added, and the reaction mixture was allowed to stand at room temperature for 192 h. The reaction mixture was filtered and evaporated. The residue was pumped in vacuo, but still contained ca. 30% starting aldehyde, so the above procedure was repeated.

The filtered reaction mixture was evaporated and to the residue water (100 ml), saturated brine (100 ml) and ethyl acetate (200 ml) were added. The aqueous phase was separated and washed with ethyl acetate (100 ml). The combined ethyl acetate extracts were washed with brine (100 ml), dried (MgSO$_4$) and evaporated. The crude title compound (2.3 g, ca. 46%) was used in the next stage, without further purification.

b.

(R)-1-[2-[[2-(4-Fluoro-2-methylphenyl)-2-(2-methylphenyl) ethenyl]oxy]ethyl]-3-piperidine carboxylic acid ethyl ester 1-[2-(2-Bromethoxy)-1-(2-methylphenyl)ethenyl]-4-fluoro-2-methylbenzene (1.15 g, 0.0033 mol), the (R)-enantiomer of ethyl nipecotate hydrochloride (see example 1) (1.92 g, 0.0099 mol) and dried potassium carbonate (2.28 g, 0.0165 mol) were stirred in acetone (100 ml) at reflux temperature for 54 h.

The cooled reaction mixture was filtered, and the filtrate was evaporated. The residue was purified by flash chromatography on silica gel (4,5 × 15 cm) eluting with heptane/ethyl acetate (9:1→4:1) to give the title compound as a gum (0.57 g, 40%), TLC rf 0.4 (SiO$_2$, ethyl acetate/heptane 1/1).

c.

(R)-1-[2-[[2-(4-Fluoro-2-methylphenyl)-2-(2-methylphenyl) ethenyl]oxy]ethyl]-3-piperidine carboxylic acid hydrochloride (R)-1-[2-[[2-(4-Fluoro-2-methylphenyl)-2-(2-methylphenyl) ethenyl]oxy]ethyl]-3-piperidine carboxylic acid ethyl ester (0.56 g, 0.0013 mol) was dissolved in ethanol (6 ml) and 10 N sodium hydroxide was introduced. After stirring the solution at room temperature for 2 h, water (200 ml) was added, and the ethanol was evaporated under reduced pressure. The aqueous solution was acidified to pH 5 with 2N hydrochloric acid solution and extracted with dichloromethane (3 × 100 ml).

The combined extracts were dried (MgSO$_4$) and evaporated to a residue which was treated with toluene (20 ml) and the mixture was filtered. To the filtrate, methanol (0.06 ml) and chlorotrimethylsilane (0.20 ml) were added, and the hydrochloride salt precipitated. Evaporation of the mixture, followed by crystallization of the residue from trace methanol/toluene provided the title compound (0.38 g, 67%), m.p. softens at 195o, melts finally at 210°.

C$_{24}$H$_{28}$FN O$_3$.HCl requires C, 66.4; H, 6.7; N, 3.2; Cl, 8.2 Found: C, 66.3; H, 6.8; N, 3.1; Cl 8.4%.

EXAMPLE 15

1-[2-[[2-(4-Fluoro-2-methylphenyl)-2-(2-methyl-phenyl) ethenyl]oxy]ethyl]-1,2,5,6-tetrahydro-3-pyridine carboxylic acid hydrochloride 1-[2-[[2-(4-Fluoro-2-methylphenyl)-2-(2-methyl-phenyl) ethenyl]oxy]ethyl]-1,2,5,6tetrahydro-3-pyridine carboxylic acid methyl ester (0.74 g, 0.0018 mol) (prepared as described in Method C) was dissolved in ethanol (15 ml) and 10 N sodium hydroxide solution (1.8 ml) was introduced. After stirring the reaction mixture for 2 h at room temperature TLC indicated that saponification was incomplete, so further 10 N sodium hydroxide solution (1.8 ml) was added, and the reaction mixture was heated for 10 min. at 40° C. Water (400 ml) was added, and the solution was extracted with diethyl ether (100 ml). The aqueous layer was acidified to pH 5 with 2N hydrochloric acid solution and extracted with dichloromethane (4 × 50 ml). The combined extracts were dried (MgSO$_4$) and evaporated to a residue (0.61 g) which was dissolved in toluene (50 ml). Methanol (0.2 ml) and chlorotrimethylsilane (0.216 ml) were added, and after mixing, a layer of cyclohexane (ca. 30 ml) was added. After storing this mixture at 4° for 18 h, the title compound was collected by filtration (0.60 g, 77%), m.p. 190°-201° (after drying in vacuo).

$C_{24}H_{26}FNO_3 \cdot HCl \cdot 0.1PhCH_3$ requires C, 67.3; H, 6.4; N, 3.2; Cl, 8.0 Found: C, 67.1; H, 6.4; N, 3.1; Cl, 8.1%

EXAMPLE 16

Method D a.

1-[2-(2-Bromoethoxy)-1-(3-fluorophenyl)ethenyl]-3-fluorobenzene bis(3-Fluorophenyl)acetaldehyde (4.82 g, 0.0208 mol) was dissolved in dichloromethane (50 ml) and tetra-n-butyl ammonium bromide (0.67 g, 0.00208 mol) was added. 12 N sodium hydroxide solution (50 ml) and 1,2-dibromoethane (17.9 ml, 0.208 mol) were introduced and the mixture was stirred vigorously at room temperature for 20 h. Dichloromethane (100 ml) and saturated brine (50 ml) were added, and the phases were separated. The aqueous phase was extracted further with dichloromethane (50 ml) and the combined dichloromethane extracts were washed with water (2 × 75 ml) and saturated brine (50 ml). Drying of the dichloromethane solution (Na$_2$SO$_4$) and evaporation provided the title compound as an oil (6.66 g, 95%), TLC rf 0.71 (SiO$_2$ dichloromethane).

b.

1-[2-[[2,2-bis(3-Fluorophenyl)ethenyl]oxy]ethyl]-1,2,5,6-tetrahydropyridine-3-carboxylic acid methyl ester hydrochloride To 1-[2-(2-Bromoethoxy)-1-(3-fluorophenyl)ethenyl]-3-fluorobenzene (6.57 g, 0.0194 mol) in acetone (100 ml) was added 1,2,5,6-tetrahydro-3-pyridine carboxylic acid methyl ester hydrochloride (guvacine methyl ester hydrochloride) (5.57 g, 0.0291 mol), dried potassium carbonate (8.03 g, 0.0581 mol) and potassium iodide (0.32 g, 0.0019 mol). The suspension was stirred at room temperature for 50 h and filtered. The filtrate was evaporated to an oil (8.2 g) which was dissolved in ethyl acetate (100 ml). Water (40 ml) was added, and the pH of the aqueous phase was adjusted to 4 with 34% aqueous tartaric acid. The aqueous layer was separated, and the organic phase was washed with pH 4 aqueous tartaric acid (20 ml), after which water (40 ml) was added. The pH of the aqueous phase was adjusted to ca. 8 with 2 N sodium hydroxide solution, and the phases were separated. The organic phase was washed with saturated brine (10 ml), dried (Na$_2$SO$_4$) and evaporated to an oil.

To this oil in toluene (20 ml) at 45° was added methanol (0.68 ml, 0.0167 mol) followed by chlorotrimethylsilane (1.173 g, 0.0156 mol). After stirring at room temperature for 18 h the ester hydrochloride had precipitated, and the suspension was cooled to 0° C. for 2 h. The solid was collected by filtration, washed with cold toluene (15 ml) and suspended in dry diethyl ether (25 ml). Filtration provided the title compound (3.56 g, 59%) as a white solid, TLC rf 0.68 (SiO$_2$:dichloromethane/methanol/acetic acid 20:2:1).

c.

1-[2-[[2,2-bis(3-Fluorophenyl)ethenyl]oxy]ethyl]-1,2,5,6-tetrahydro-3-pyridine carboxylic acid hydrochloride To 1-[2-[[2,2-bis(3-Fluorophenyl)ethenyl]oxy]ethyl]-1,2,5,6-tetrahydro-3-pyridine carboxylic acid methyl ester hydrochloride (3.50 g, 0.0078 mol) in 96% aqueous ethanol (25 ml) at 5° was added 12 N sodium hydroxide solution (2.1 ml). After stirring the solution at room temperature for 4.5 h the pH was adjusted to 6 with 4 N hydrochloric acid solution, and the mixture was evaporated to an oil. Ethyl acetate (50 ml) and water (20 ml) were added, and the organic phase was separated. The aqueous phase was washed with ethyl acetate (25 ml) and the combined organic phases were washed with saturated brine (10 ml). The ethyl acetate phase was dried (Na$_2$SO$_4$) and the residue was co-evaporated with dichloromethane (3 × 15 ml).

To the residue in toluene (22 ml) at 45° was added methanol (0.225 ml) and chlorotrimethylsilane (0.705 ml). On cooling and stirring at room temperature for 18 h the product hydrochloride had precipitated, and the suspension was cooled to 0° for 1.5 h. The solid was collected by filtration and dried in vacuo to give the desired product (2.65 g, 80%). Recrystallization from water provided the title compound (1.60 g, 53%), m.p. 158°-9°.

$C_{22}H_{21}F_2NO_3 \cdot HCl \cdot 0.3H_2O$ requires C, 61.8; H, 5.1; N, 3.3; Cl, 8.3 Found: C, 61.5; H, 5.3; N, 3.1; Cl, 8.4%.

EXAMPLE 17

(R)-1-[2-[[2,2-bis(2-Methylphenyl)ethenyl]oxy]ethyl]-3-piperidine carboxylic acid hydrochloride (R)-1-[2-[[2,2-bis(2-Methylphenyl)ethenyl]oxy]ethyl]-3-piperidine carboxylic acid ethyl ester (2.20 g, 0.0054 mol) (prepared as described in Method D) was dissolved in ethanol (20 ml) and 10 N sodium hydroxide solution (7 ml) was introduced. After stirring the solution at room temperature for 3 h, water (300 ml) was added, and the solution was washed with diethyl ether (100 ml). The aqueous layer was washed further with diethyl ether (100 ml). The pH of the aqueous layer was adjusted to 5 and then extracted with dichloromethane (4 × 100 ml). The combined extracts were dried (MgSO$_4$), evaporated, and the residue was dissolved in toluene (50 ml). Methanol (0.4 ml) and chlorotrimethylsilane (0.7 ml) were added, and the product precipitated This solid was collected by filtration and recrystallized from water to give the title compound (1.4 g, 62%), m.p. 217°-226° (after drying in vacuo).

$C_{24}H_{29}NO_3 \cdot HCl$ requires C, 69.3; H, 7.3; N, 3.4; Cl, 8.5 Found: C, 69.4; H, 7.4; N, 3.3; Cl, 8.5%.

EXAMPLE 18

(R)-1-[2-[[2,2-bis(4-Fluoro-2-methylphenyl)ethenyl]oxy]-ethyl]-3-piperidine carboxylic acid hydrochloride (R)-1-[2-[[2,2-bis(4-Fluoro-2-methylphenyl)ethenyl]oxy]-ethyl]-3-piperidine carboxylic acid ethyl ester (1.72 g, 0.0039 mol) (prepared as described in Method D) was dissolved in ethanol (20 ml) and 10 N sodium hydroxide solution (4 ml) was introduced. The solution was stirred at room temperature for 3 h and water (100 ml) was added. The solution was extracted with diethyl ether (2 × 100 ml) and the aqueous phase was acidified to pH 5 with 2 N hydrochloric acid solution. Extraction with dichloromethane (4 × 80 ml) and drying of the combined extracts (MgSO$_4$) followed by evaporation gave a residue, which was dissolved in toluene (50 ml). Methanol (0.16 ml) and chlorotrimethylsilane (0.51 ml) were added, and the product precipitated. The mixture was evaporated to a solid and recrystallized from toluene to give the title compound as a white crystalline solid (0.78 g, 44%), m.p. 175°–185° (decomp.)

$C_{24}H_{27}FNO_3 \cdot HCl$ requires C, 63.8; H, 6.2; N, 3.1; Cl, 7.8 Found: C, 64.1; H, 6.3; N, 3.0; Cl, 7.3%

EXAMPLE 19

E or Z-(R)-1-[2-[[2-(3-Methoxyphenyl)-2-(2-methylphenyl)ethenyl]oxy]ethyl]-3-piperidine carboxylic acid hydrochloride E or Z-(R)-1-[2-[[2-(3-Methoxyphenyl)-2-(2-methylphenyl) ethenyl]oxy]ethyl]-3-piperidine carboxylic acid ethyl ester (0.50 g, 0.0012 mol) (prepared as described in Method D) was dissolved in ethanol (15 ml) and 12 N sodium hydroxide solution (0.2 ml) was introduced. After stirring the solution at room temperature for 6 h, ice (100 g) was added, and the pH of the reaction mixture was adjusted to ca. 7 with 37% hydrochloric acid solution Dichloromethane (200 ml) was added, and the pH was further adjusted to <2 with 37% hydrochloric acid solution. The dichloromethane phase was dried (Na$_2$SO$_4$) and evaporated to a solid (0.3 g, 60%), m.p. 188°–192°

$C_{24}H_{29}NO_4 \cdot HCl \cdot 0.25H_2O$ requires C, 66.0; H, 7.0; N, 3.2; Cl, 8.2 Found: C, 66.1; H, 7.2; N, 3.1; Cl, 8.1%.

EXAMPLE 20

E or Z-(R)-1-[2-[[2-(3-Methoxyphenyl)-2-(2-methylphenyl)ethenyl]oxy]ethyl]-3-piperidine carboxylic acid hydrochloride E or Z-(R)-1-[2-[[2-(3-Methoxyphenyl)-2-(2-methylphenyl) ethenyl]oxy]ethyl]-3-piperidine carboxylic acid ethyl ester (0.80 g, 0.0019 mol) (opposite geometric isomer of example 19) was dissolved in ethanol (15 ml) and 12 N sodium hydroxide solution (0.3 ml) was introduced. After stirring the solution at room temperature for 6 h, ice (50 g) was added, and the pH of the reaction mixture was adjusted to ca. 7 with 37% hydrochloric acid solution. Dichloromethane (200 ml) was added, and the pH was further adjusted to <2 with 37% hydrochloric acid solution. The dichloromethane phase was dried (Na$_2$SO$_4$) and evaporated to a solid (0.35 g, 44%), m.p. 198°–202°.

$C_{24}H_{29}NO_4 \cdot HCl$ requires C, 66.7; H, 7.0; N, 3.2; Cl, 8.2 Found: C, 66.5; H, 7.2; N, 3.0; Cl, 7.6.

EXAMPLE 21

1-[2-[[2-(3-Methoxyphenyl)-2-(2-methylphenyl)ethenyl]oxy]-ethyl]-1,2, 5,6-tetrahydro-3-pyridine carboxylic acid hydrochloride 1-[2-[[2-(3-Methoxyphenyl)-2-(2-methylphenyl)ethenyl]oxy]-ethyl]-1, 2,5,6-tetrahydro-3-pyridine carboxylic acid methyl ester (1.15 g, 0.0027 mol) (prepared as described in Method D) was dissolved in ethanol (15 ml) and 12 N sodium hydroxide solution (0.5 ml) was introduced. After stirring the solution at room temperature for 4 h, ice (30 g) was added, and the pH of the reaction mixture was adjusted to ca. 7 with 37% hydrochloric acid solution. Dichloromethane (200 ml) was added, and the pH was further adjusted to ca. 1 with 37% hydrochloric acid solution. Water was added until the solid material was dissolved, and the dichloromethane phase was dried (Na$_2$SO$_4$) and evaporated to an oil, which was co-evaporated three times with acetone. The residue was triturated with diethyl ether to give the title compound (0.60 g, 52%), which gave HPLC retention times of 17.1 and 17.6 min. for the geometric isomers (gradient elution, water/20-80% acetonitrile, both containing 0.1% TFA).

$C_{24}H_{28}NO_4 \cdot 0.8HCl \cdot 0.8H_2O$ requires C, 65.8; H, 7.0; N, 3.2; Cl, 6.3 Found: C, 65.3; H, 7.0; N, 3.2; Cl, 6.9%.

EXAMPLE 22

1-[2-[[2-(3-Chlorophenyl)-2-(2-methylphenyl)ethenyl]oxy]-ethyl]-1, 2,5,6-tetrahydro-3-pyridine carboxylic acid hydrochloride 1-[2-[[2-(3-Chlorophenyl)-2-(2-methylphenyl)ethenyl]oxy]-ethyl]-1,2, 5,6-tetrahydro-3-pyridine carboxylic methyl ester (0.60 g, 0.0014 mol) (prepared as described in Method D) was dissolved in ethanol (5 ml) and 12 N sodium hydroxide solution (0.35 ml) was introduced. After stirring the solution at room temperature for 3 h, 37% hydrochloric acid solution was added, until the pH was measured as ca. 1. Dichloromethane (200 ml) was introduced, and the mixture was dried (Na$_2$SO$_4$), filtered and evaporated to a residue, which was co-evaporated twice with acetone. The residue was recrystallized from acetone/ethyl acetate to give the title compound (0.33 g, 55%) as white crystals, m.p. 168°–170° HPLC retention times 16.12 and 18.42 for the geometric isomers (gradient elution, water/20–80% acetonitrile, both phases containing 0.1% TFA).

E or Z-1-[2-[[2-(3-Chlorophenyl)-2-(2-methylphenyl)ethenyl]oxy]ethyl]-1,2,5, 6-tetrahydro-3-pyridine carboxylic acid hydrochloride E or Z-1-[2-[[2-(3-Chlorophenyl)-2-(2-methylphenyl))ethenyl]oxy]ethyl]-1,2, 5,6-tetrahydro-3-pyridine carboxylic acid methyl ester (0.55 g, 0.0013 mol) (prepared as described in Method D) was dissolved in ethanol (5 ml) and 12 N sodium hydroxide solution (0.33 ml) was introduced. After stirring the solution at room temperature for 3 h, 37% hydrochloric acid solution was added until the pH was measured as ca. 1. Dichloromethane (200 ml) was introduced, and the mixture was dried (Na$_2$SO$_4$), filtered and evaporated to a residue, which was co-evaporated twice with acetone. Recrystallization from acetone/ethyl acetate provided the title compound (0.17 g, 30%) as a white solid, m.p. 214°–215°.

$C_{23}H_2ClNO_3 \cdot HCl$ requires C, 63.6; H, 5.8; N, 3.2; Cl, 8.2 Found: C, 63.2; H, 5.8; N, 3.4; Cl, 8.0%.

EXAMPLE 23

1-[2-[[2,2-bis(2-Ethylphenyl)ethenyl]oxy]ethyl]-1,2,5,6-tetrahydro-3-pyridine carboxylic acid hydrochloride 1-[2-[[2,2-bis(2-Ethylphenyl)ethenyl]oxy]ethyl]-1,2,5,6-tetrahydro-3-pyridine carboxylic acid methyl ester (1.40 g, 0.00323 mol) (prepared as described in Method D) was dissolved in ethanol (10 ml) and 12 N sodium hydroxide solution (0.8 ml) was introduced. After stirring the solution at room temperature for 5 h, 37% hydrochloric acid solution was added until the pH was measured as ca. 1. Dichloromethane (250 ml) was introduced, and the mixture was dried (Na$_2$SO$_4$), filtered and evaporated to a residue, which was co-evaporated with acetone. Recrystallization from acetone provided the title compound (0.80 g, 57%) as a white solid, m.p. 162°–165°.

C$_{26}$H$_{31}$NO$_3$.HCl requires C, 70.7; H, 7.3; N, 3.2; Cl, 8.0 Found: C, 70.5; H, 7.4; N, 3.6; Cl, 8.0%.

EXAMPLE 24

(R)-1-[2-[[2,2-bis(2-Ethylphenyl)ethenyl]oxy]ethyl]-3-piperidine carboxylic acid hydrochloride (R)-1-[2-[[2,2-bis(2-Ethylphenyl)ethenyl]oxy]ethyl]-3-piperidine carboxylic acid ethyl ester (1.20 g, 0.00275 mol) (prepared as described in Method D) was dissolved in ethanol (10 ml) and 12 N sodium hydroxide solution (0.7 ml) was introduced. After stirring the solution at room temperature for 5 h, 37% hydrochloric acid solution was added until the pH was measured as ca. 1. Dichloromethane (250 ml) was introduced, and the mixture was dried (Na$_2$SO$_4$), filtered and evaporated to a residue, which was co-evaporated with acetone. Recrystallization from acetone provided the title compound (0.85 g, 70%) as a white solid, m.p. 205°–206°.

C$_{26}$H$_{33}$NO$_3$.HCl requires C, 70.3; H, 7.7; N, 3.2; Cl, 8.0 Found: C, 70.0; H,7.8; N, 3.4; Cl, 7.9%.

EXAMPLE 25

1-[2-[[2,2-Diphenylethenyl]oxy]ethyl]-1,2,5,6-tetrahydro-3-pyridine carboxylic acid hydrochloride 1-[2-[[2,2-Diphenylethenyl]oxy]ethyl]-1,2,5,6-tetrahydro-3-pyridine carboxylic acid methyl ester (4.33 g, 0.01147 mol) (prepared as described in Method D) was dissolved in ethanol (50 ml) and 10 N sodium hydroxide solution (11.5 ml) was introduced, followed by water (5 ml). The solution was stirred at room temperature for 2.5 h and stored at 4° C. for 18 h. 2 N hydrochloric acid solution was added until the pH reached ca. 2, and the mixture was extracted with dichloromethane (3 × 60 ml). The combined extracts were dried (MgSO$_4$) and evaporated to give a foam (4.24 g) which was crystallized from 2-propanol to provide the title compound (2.32 g, 52%) as a white solid, m.p. 173°–176°.

C$_{22}$H$_{23}$NO$_3$.HCl.0.2H$_2$O requires C, 67.8; H, 6.3; N, 3.6; Cl, 9.1 Found: C, 67.7; H, 6.3; N, 3.4; Cl, 8.8%.

EXAMPLE 26

1-[2-[[2-(2-Fluorophenyl)-2-(2-methylphenyl)ethenyl]oxy]-ethyl]-1,2, 5,6-tetrahydro-3-pyridine carboxylic acid hydrochloride 1-[2-[[2-(2-Fluorophenyl)-2-(2-methylphenyl)ethenyl]oxy]-ethyl]-1,2, 5,6-tetrahydro-3-pyridine carboxylic acid methyl ester hydrochloride (2.18 g, 0.0049 mol) (prepared as described in Method D) was dissolved in ethanol (24 ml) and 12 N sodium hydroxide solution (1.83 ml) was introduced at 5°. The solution was stirred at room temperature for 2.5 h and stored at −10° for 18 h. The reaction mixture was evaporated to a residue after the pH had been adjusted to 6.5 with 4 N hydrochloric acid solution. Water (20 ml) and ethyl acetate (50 ml) were added, the aqueous layer was separated and extracted again with ethyl acetate (25 ml). The combined ethyl acetate extracts were washed with saturated brine (40 ml), dried (M ) and evaporated to a residue, which was co-evaporated with dichloromethane (3 × 40 ml). This residue (1.9 g) was dissolved in toluene (15 ml) and methanol (0.2 ml) was introduced followed by chlorotrimethylsilane (0.62 ml). The mixture was stirred for 18 h at room temperature and cooled to 0° for 2 h. The title compound (1.9 g, 91%) was obtained as white crystals, m.p. 183°–5°, after drying in vacuo.

C$_{23}$H$_{24}$FNO$_3$.1.25HCl requires C, 64.7; H, 6.0; N, 3.3; Cl, 10.4 Found: C, 64.3; H, 6.0; N, 3.1; Cl, 9.9%

EXAMPLE 27

1-[2-[[2-(2,4-Dichlorophenyl)-2-(2-methylphenyl)ethenyl]-oxy]ethyl]-1,2, 5,6-tetrahydro-3-pyridine carboxylic acid hydrochloride 1-[2-[[2-(2,4-Dichlorophenyl)-2-(2-methylphenyl)ethenyl]-oxy]ethyl]-1,2, 5,6-tetrahydro-3-pyridine carboxylic acid methyl ester hydrochloride (2.76 g, 0.0055 mol) (prepared as described in Method D) was dissolved in ethanol (30 ml) and 12 N sodium hydroxide solution (2.1 ml) was introduced at 5°. The solution was stirred at room temperature for 3 h and stored at −10° for 18 h. The reaction mixture was evaporated to a residue after the pH had been adjusted to 6.5 with 4 N hydrochloric acid solution. Water (50 ml), ethyl acetate (50 ml) and dichloromethane (50 ml) were added and the organic phase was separated. The aqueous phase was further extracted with ethyl acetate (50 ml) dichloromethane (50 ml) and the combined organic extracts were dried (MgSO$_4$) and evaporated. The resultant residue was co-evaporated twice with methanol and twice with carbon tetrachloride to give a foam (2.7 g).

This foam was dissolved in toluene (20 ml) and methanol (0.23 ml) was introduced followed by chlorotrimethylsilane (0.71 ml) at 35°. The product began to crystallize at around 40° and the mixture was stirred for 18 h at room temperature and cooled to 0° C. for 2 h. The title compound (2.20 g, 84%) was obtained as white crystals, m.p. 187°–90° (decomp.) after drying in vacuo.

C$_{23}$H$_{23}$Cl$_2$O$_3$.1.1HCl requires C, 58.5; H, 5.2; N, 3.0; Cl 8.3 Found: C, 58.2; H, 5.1; N, 2.8; Cl, 8.1%.

EXAMPLE 28

1-[2-[[2,2-bis(2-Chlorophenyl)ethenyl]oxy]ethyl]-1,2,5,6-tetrahydro-3-pyridine carboxylic acid hydrochloride 1-[2-[[2,2-bis(2-Chlorophenyl)ethenyl]oxy]ethyl]-1,2,5,6-tetrahydro-3-pyridine carboxylic acid methyl ester hydrochloride (3.60 g, 0.0075 mol) (prepared as described in Method D) was dissolved in ethanol (40 ml) and 12 N sodium hydroxide solution (2.5 ml) was introduced at 5°. The solution was stirred at room temperature for 6 h and stored at −10° for 18 h. The reaction mixture was evaporated to a residue after the pH had been adjusted to 6.5 with 4 N hydrochloric acid solution. Water (10 ml) and ethyl acetate (50 ml) were added, and the ethyl acetate was separated. The ethyl acetate phase was washed with saturated brine (10 ml) dried (Na$_2$SO$_4$) and evaporated. The resultant residue was evaporated to give a foam (3.1 g). This foam was dissolved in toluene (23 ml) and methanol (0.30 ml) was introduced followed by chlorotrimethylsilane e (0.94 ml) at 35°. The product began to crystallize at around 40° and the mixture was stirred for 48 h at room temperature and cooled to 0° C. for 2 h. The title compound (2.5 g, 73%) was obtained as white crystals, m.p. 200°–203° (decomp.). TLC rf 0.16 (SiO$_2$, dichloromethane/methanol/acetic acid: 80/8/4).

EXAMPLE 29

1-[2-[[2,2-bis(4-Fluoro-2-methylphenyl)ethenyl]oxy]ethyl]-1,2, 5,6-tetrahydro-3-pyridine carboxylic acid hydrochloride 1-[2-[[2,2-bis(4-Fluoro-2-methylphenyl)ethenyl]oxy]ethyl]-1, 2,5,6-tetrahydro-3-pyridine carboxylic acid ethyl ester (1.27 g, 0.0029 mol) (prepared as described in Method D) was dissolved in ethanol (30 ml) and 10 N sodium hydroxide solution (10 ml) was introduced. After stirring the solution at room temperature for 1 h, water (500 ml) was added and the solution was washed with diethyl ether (2 × 100 ml). The pH of the aqueous layer was adjusted to 5 using 2 N hydrochloric acid solution and extracted with dichloromethane (3 × 200 ml). The combined extracts were dried (MgSO$_4$), evaporated and the residue was dissolved in toluene (50 ml), and added to a solution of chlorotrimethylsilane (0.47 ml) and methanol (0.15 ml) in toluene (100 ml). The precipitate was collected by filtration after the mixture had been stored at room temperature for 18 h. This solid was recrystallized three times from toluene/trace methanol to give the title compound (0.85 g, 65%) as white crystals, m.p. 195°-20° (decomp.).

$C_{24}H_{25}F_2NO_3 \cdot HCl \cdot 0.2H_2O$ requires C, 63.6; H, 5.9; N, 3.1; Cl, 7.9. Found: C, 63.6; H, 5.9; N, 3.1; Cl, 7.9%.

EXAMPLE 30

(R)-1-[2-[[2-(2-Chlorophenyl)-2-(2-methylphenyl)ethenyl]oxy]ethyl]-3-piperidine carboxylic acid hydrochloride (R)-1-[2-[[2-(2-Chlorophenyl)-2-(2-methylphenyl)ethenyl]oxy]ethyl]-3-piperidine carboxylic acid ethyl ester (4.1 g, 0.0096 mol) (prepared as described in Method D) was dissolved in ethanol (100 ml) and 18 N sodium hydroxide solution (10 ml) was introduced. After stirring the solution at room temperature for 1 h water (500 ml) was added, and the solution was washed with diethyl ether (2 × 100 ml). The pH of the aqueous phase was adjusted to 1 using 2 N hydrochloric acid solution and extracted with dichloromethane (4 × 200 ml). The combined extracts were dried (M ), evaporated and the residue was crystallized from toluene/trace methanol to provide the title compound (3.47 g, 87%) as a white crystalline solid, m.p. 231°-234°.

$C_{23}H_{26}ClNO_3 \cdot HCl$ requires C, 63.3; H, 6.2; N, 3.2; Cl, 16.3. Found: C, 63.2; H, 6.4; N, 3.1; Cl, 16.3%.

EXAMPLE 31

1-[2-[[(2-(2-Chlorophenyl)-2-(2-methylphenyl)ethenyl]oxy]-ethyl]-1,2, 5,6-tetrahydro-3-pyridine carboxylic acid hydrochloride 1-[2-[[(2-(2-Chlorophenyl)-2-(2-methylphenyl)ethenyl]oxy]-ethyl]-1,2, 5,6-tetrahydro-3-pyridine carboxylic acid ethyl ester (3.35 g, 0.0079 mol) (prepared as described in Method D) was dissolved in ethanol (100 ml) and 18 N sodium hydroxide solution (10 ml) was introduced. After stirring the solution at room temperature for 2 h, water (500 ml) was added, and the reaction mixture was washed with diethyl ether (2 × 100 ml). The pH of the aqueous phase was adjusted to 1 using 2 N hydrochloric acid solution and it was extracted with dichloromethane (4 × 100 ml). The combined extracts were dried (MgSO$_4$), evaporated and the solid residue was recrystallized from toluene/trace methanol to provide the title compound (2.2 g, 64%) as a white crystalline solid, m.p. 196°-198°.

$C_{23}H_2ClNO_3 \cdot HCl$ requires C, 63.6; H, 5.8; N, 3.2; Cl, 16.3. Found: C, 63.6; H, 5.9; N, 3.1; Cl, 16.3%.

EXAMPLE 32

(R)-1-[3-[[2,2-bis(4-Fluorophenyl)ethenyl]oxy]propyl]-3-piperidine carboxylic acid hydrochloride (R)-1-[3-[[2,2-bis(4-Fluorophenyl)ethenyl]oxy]propyl]-3-piperidine carboxylic acid ethyl ester tartrate (3.8 g, 0.0065 mol) (prepared as described in Method D) was dissolved in ethanol (25 ml) and 12 N sodium hydroxide solution (2.2 ml) was introduced at 5° After stirring the solution at room temperature for 4.8 h, the pH of the reaction mixture was adjusted to ca. 7 with 4 N hydrochloric acid solution, and the mixture was evaporated to a residue in vacuo. Water (25 ml) was added, and the mixture was extracted with dichloromethane (3 × 50 ml). The combined extacts were dried (MgSO$_4$) and evaporated to a foam, which was dissolved in toluene (1.5 ml) and warmed to 40° Methanol (0.27 ml) was introduced followed by chlorotrimethylsilane (0.83 ml). The product precipitated slowly, and after the suspension had been allowed to stand for 18 h at room temperature it was collected by filtration. The title compound (2.9 g, quant.) was obtained as white crystals, m.p. 177°-180° (after drying in vacuo). HPLC retention time 12.55 (gradient elution, water/35-50% acetonitrile, aqueous phase containing 0.1 M ammonium sulphate solution).

EXAMPLE 33

Method E (R)-1-[2-[[2,2-Diphenylethyl]oxy]ethyl]-3-piperidine carboxylic acid (R)-1-[2-[[2,2-Diphenylethyl]oxy]ethyl]-3-piperidine carboxylic acid hydrochloride (120 mg, 0.31 mmol) was dissolved in methanol (5 ml) and stirred under an atmosphere of hydrogen for 2 h at room temperature in the presence of 5% palladium on carbon catalyst (52% aqueous paste) and then filtered. The filtrate was evaporated to dryness leaving a residue, which was dissolved in water. The aqueous solution was lyophilized to give the title compound (80 mg, 58% of the theoretical yield) as a solid, TLC rf 0.32 (SiO$_2$, methanol).

We claim:

1. A compound which is (R)-1-3-piperidine carboxylic acid or a pharmaceutically acceptable salt thereof.

2. A pharmaceutical composition suitable for use as an analgesic, anxiolytic, antidepressant, hypnotic and for treating epilepsy and muscular and movement disorders, comprising (a) the compound according to claim 1 or a pharmaceutically acceptable salt thereof together with (b) a pharmaceutically acceptable carrier or diluent.

3. The pharmaceutical composition according to claim 2 in the form of a dosage unit containing between 0.5 mg and 1000 mg of the compound (a).

4. A method of treating epilepsy, muscular and movement disorders, pain, anxiety, depression and sleeping disorders in a subject in need of such treatment comprising administering to said said subject an effective amount of the compound according to claim 1 or a pharmaceutically acceptable salt thereof together with a pharmaceutically acceptable carrier or diluent.

5. The method of claim 4, wherein the compound (a) is administered in the form of a pharmaceutical composition together with a pharmaceutically acceptable carrier or diluent.

* * * * *